United States Patent [19]

Hachey et al.

[11] Patent Number: 4,918,974

[45] Date of Patent: Apr. 24, 1990

[54] METHOD AND APPARATUS FOR THE MEASUREMENT OF THE THERMAL CONDUCTIVITY OF GASES

[75] Inventors: Raynald Hachey, Shipshaw; Daniel Lamarre, Duberger; Jacques Marcotte, Jonquiere, all of Canada

[73] Assignee: Alcan International Limited, Montreal, Canada

[21] Appl. No.: 307,318

[22] Filed: Feb. 6, 1989

[51] Int. Cl.$^5$ ............................................. G01N 25/36
[52] U.S. Cl. ..................................................... 73/27 R
[58] Field of Search ..................... 73/27 R, 19; 338/34

[56] References Cited

U.S. PATENT DOCUMENTS

| | | | |
|---|---|---|---|
| 3,864,959 | 2/1975 | MacDonald | 73/27 R |
| 4,185,491 | 1/1980 | Owen | 73/27 R |
| 4,461,166 | 7/1984 | Gatten et al. | 73/27 R |
| 4,498,330 | 2/1985 | Hosoya | 73/27 R X |
| 4,533,520 | 8/1985 | Bossart et al. | 73/27 R X |
| 4,541,988 | 9/1985 | Tozier et al. | 73/27 R X |
| 4,685,325 | 8/1987 | Warchol | 73/19 |
| 4,829,810 | 5/1989 | Anderson et al. | 73/27 R |

Primary Examiner—Hezron E. Williams
Assistant Examiner—Joseph W. Roskos
Attorney, Agent, or Firm—Cooper & Dunham

[57] ABSTRACT

A new method and apparatus for the measurement of thermal conductivity of gases employs a single katharometer element, which preferably is a thermistor, but may be a heated filament. In a preferred circuit the element is part of a first potential divider whose output voltage is compared to that of a second reference potential divider by applying them to the inputs of a differential amplifier supplying heating current to the element. If the temperature of the element changes, changing its resistance, the amplifier output changes the amount of power supplied to the katharometer element to restore it to the predetermined temperature. Passage of a gas with a different thermal characteristic over the element changes its temperature which is corrected by the circuit so that the element operates at a constant temperature. The output of the amplifier to maintain the constant temperature is therefore a measure of the gas thermal conductivity. Operation of the apparatus is therefore independent of the resistance/temperature characteristic of the thermal element and is virtually insensitive to ambient temperature changes. The invention also provides new methods of operating katharometers to reduce the sensitivity of measurement to thermal leakage, to reduce the deleterious effect of temperature changes to the Katharometer, and to provide a simple but effective model for their operation.

18 Claims, 2 Drawing Sheets

METHOD AND APPARATUS FOR THE MEASUREMENT OF THE THERMAL CONDUCTIVITY OF GASES

FIELD OF THE INVENTION

This invention is concerned with new methods and new apparatus for the measurement of the thermal conductivity of gases. It is concerned particularly but not exclusively with such methods and apparatus for the measurement of the composition of gas mixtures by measurement of their thermal conductivity, as employed in the measurement of the gas content of molten metal.

REVIEW OF THE PRIOR ART

A commercially important application of the measurement of gas thermal conductivity is the determination of the amount of gas, particularly hydrogen, in a body of molten metal, particularly aluminum and its alloys. The presence of more than a predetermined small amount of hydrogen (e.g. 0.1–0.15 ml $H_2$ per 100 g metal) can have deleterious effects on the properties of the metal, and accurate measurement is therefore necessary to ensure that the content is below this value.

One type of katharometer apparatus commonly employed hitherto uses two cells electrically connected as two opposed arms of a resistance bridge, one of the cells receiving or containing a reference gas and constituting a reference cell, while the other receives a stream of the gas to be measured and constitutes the measuring cell. Each cell contains a fine heated platinum wire whose resistance depends upon its temperature, the amount by which the wire is cooled upon passage of the gas through the cell depending upon the gas thermal conductivity, which will usually vary with the gas composition because of the different values for the different gases. The resultant change in the resistance of the measuring cell unbalances the bridge, and the value of the resulting unbalance voltage is a function of the thermal conductivity of the gas under test.

In practice a suitable porous probe, such as that disclosed in U.S. patent application Ser. No. 07/199,673, the disclosure of which is incorporated herein by this reference, is immersed in the molten metal and a carrier gas such as nitrogen is passed through it. Gases dissolved in the metal are entrained in the carrier gas in proportion to their concentration in the metal, and if the thermal conductivities of the entrained and carrier gases are sufficiently different, then measurement of this parameter for the carrier gas alone and for the resultant mixture can be used to determine the concentration of the gas dissolved in the metal.

The manufacture and operation of katharometer apparatus to give consistent results presents a number of difficulties. It is difficult in the first place to produce commercially two katharometer cells with sufficiently similar static and dynamic characteristics to provide a bridge that can be balanced without the need for static and dynamic correcting circuit elements. The two cells should be kept as closely as possible at the same temperature, but this is difficult to achieve when the filament of the measurement cell inherently varies in temperature to provide the necessary unbalance. It is usual therefore to try to maintain the two cells at some standard temperature so as to match their responses as closely as possible. A typical range of hydrogen gas concentration in molten aluminum is 0.1 to 0.3 ml$H_2$/100 g corresponding to 1%–9% by volume in the carrier gas, but it is possible for the percentage to be as high as 25%, and it is not unknown for this type of katharometer to be unable to measure values above 0.4, so that accurate measurement of these higher values becomes impossible.

An attempt has been made to avoid this problem by providing a katharometer using a single cell. U.S. Pat. No. 4,685,325 discloses such a single cell katharometer which is supplied with current from a constant current source to heat the filament. A balancing circuit is connected across the cell to balance the current against this constant current source, so that the output voltage is zero when the carrier gas alone is passing through the cell. With such an arrangement when the mixture of carrier and entrained hydrogen gases is applied to the cell the voltage change developed across the filament is a function of the proportion of hydrogen in the carrier gas, and thus in the molten metal.

DEFINITION OF THE INVENTION

It is the principal object of the present invention to provide a new method for the measurement of gas thermal conductivity.

It is another principal object to provide a new apparatus for such measurement employing a single temperature sensitive element.

In accordance with the present invention there is provided a method for the measurement of gas thermal conductivity including:

passing a gas whose conductivity is to be measured over an element having a temperature/resistance characteristic to thereby change the temperature of the element from a predetermined value and thereby change its resistance from a corresponding value;

employing the change of resistance of the element to change the supply of electrical power to the element to restore its temperature to the predetermined value and its resistance to the corresponding value; and measuring the amount of power supplied to the element to determine the gas thermal conductivity.

Also in accordance with the invention there is provided a new apparatus for the measurement of gas thermal conductivity comprising:

an element having a temperature/resistance characteristic;

means for supplying electric power to the element to heat it;

means for supplying a gas whose conductivity is to be measured to the element to thereby change the temperature of the element from a predetermined value and thereby change its resistance from a corresponding value;

control means responsive to the change of resistance to change the amount of electric power supplied to the element to maintain its temperature at the predetermined value and its resistance at the corresponding value; and means for measuring the amount of power required to maintain the element at its predetermined temperature to provide a measurement representative of the thermal conductivity of the gas.

Further in accordance with the invention there is provided a method for the operation of a katharometer employing an element having a temperature/resistance characteristic and having electrical leads, wherein heat leakage from the leads will affect the sensitivity of measurement by the katharometer, the method including mounting the leads on respective isothermal heat sinks to stabilize the leakage thermal resistance thereof.

Further in accordance with the invention there is provided a katharometer comprising an element having a temperature/resistance characteristic and having electrical leads, wherein heat leakage from the leads will affect the sensitivity of measurement by the katharometer, wherein the leads are mounted on respective isothermal heat sinks to stabilize the leakage thermal resistance thereof.

Further in accordance with the invention there is provided a method of operating a katharometer employing two measurements spaced in time to determine the proportion of gas dissolved in molten metal, the method including circulating a carier gas through the katharometer and a probe immersed in the molten metal for a first period of time sufficient to entrain the gas to be determined in the carrier gas to form a mixture of gases, and thereafter making a first measurement;

and thereafter purging the katharometer with carrier gas to remove the gas mixture and making a second measurement within a short period of time after the first measurement.

Further in accordance with the invention there is provided a method of operating a katharometer to obtain the thermal conductivity $K_m$ of gas, the katharometer employing an element having a temperature/resistance characteristic and that is exposed to the cooling effect of the gas, comprising the step of measuring the power required to maintain the element at a predetermined temperature and then determining the value of $K_m$ by the relation:

$$\text{POWER} = \frac{1}{G} \cdot (T_t - T_b) \cdot \left[ K_e + \frac{K_i \cdot K_m}{(K_i + K_m)} \right]$$

where:

G is a geometrical constant of the katharometer.
$T_t$ is the temperature of the element;
$T_b$ is the temperature of the katharometer body;
$K_1$ is an equivalent gas thermal conductivity corresponding to heat loss by the element electrical leads;
$K_i$ is the equivalent gas thermal conductivity corresponding to the thermal resistivity of the element; and
$K_m$ is the thermal conductivity of the gas to be determined.

DESCRIPTION OF THE DRAWINGS

Particular preferred embodiments of the invention will now be described, by way of example, with reference to the accompanying drawings, wherein.

DESCRIPTION OF THE PREFERRED EMBODIMENTS

Figure 1:
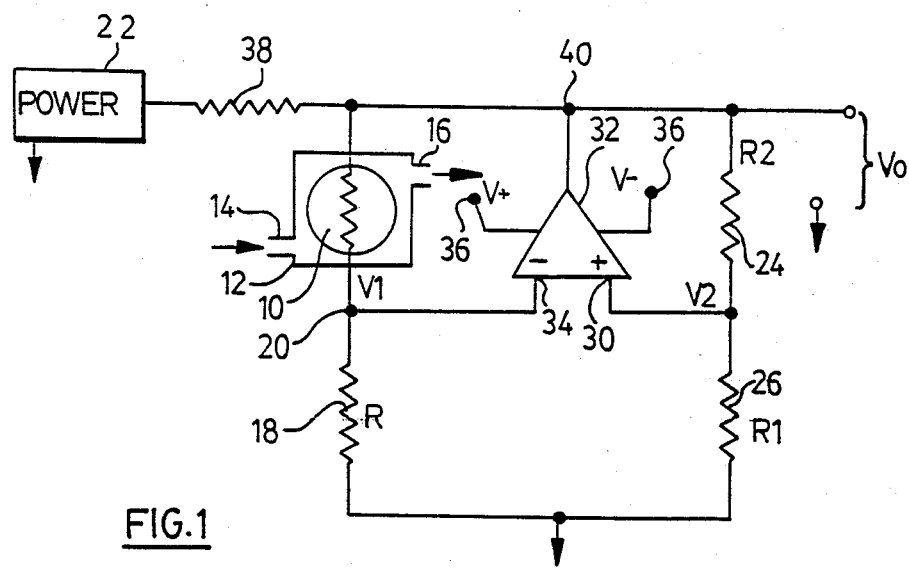
FIG. 1 is a schematic circuit diagram of one embodiment.

The apparatus of the invention employs a temperature sensitive resistance device 10, i.e. a device whose electrical resistance varies with its absolute temperature, with the absolute value of its resistance being sufficiently constant for a predetermined temperature value. In the embodiments illustrated the device is a thermistor of suitable temperature/resistance characteristic and is mounted in the usual relatively heavy metal katharometer enclosure 12 having a gas inlet 14 and a gas outlet 16, so that a stream of the test gas whose thermal conductivity is to be measured can be passed through the enclosure interior. Alternatively the element 10 can be a heated filament. The element is connected in series with a fixed resistor 18 to provide a first potential divider having a junction 20 at which a voltage $V_1$ will appear, the divider being supplied with electric power from a source 22.

Two series-connected fixed resistors 24 and 26 constituting a second reference potential divider are also supplied from the source 22 and their junction 28 is connected to one input terminal 30 of a differential amplifier 32 so as to apply a reference voltage $V_2$ thereto, the junction 20 being connected to the other amplifier input terminal 34. The amplifier is supplied with power from terminals 36 and a start-up load resistor 38 is connected between the source 22 and the circuit to set the start-up voltage (positive or negative) that is applied to the cell.

The thermistor 10 will be heated by the current passing through it and as its temperature increases its resistance decreases, decreasing the value of $V_1$. If the potentials $V_1$ and $V_2$ are not equal the amplifier 32 produces a change in its output voltage proportional to their difference that heats the element 10 further, and thus further decreases its resistance until balance is reached, at which point the element is at a steady temperature and corresponding steady resistance value. In this steady state a constant voltage $V_o$ will be produced at the output terminal 40 of the amplifier. If a stream of a gas of higher thermal conductivity is now introduced into the katharometer the element 10 cools resulting in an increase in its electrical resistance so that $V_1$ decreases, which results in an increase in the voltage $V_o$ and an increase in the current through the element and resistor 18 to increase the electric power (energy per second) supplied to the element until its temperature and resistance are restored to the predetermined values. The new value of the voltage $V_o$ is correlated with the gas thermal conductivity of the mixture of gases in the stream by the relation:

$$V_0^2 = \frac{R}{G} \cdot \frac{(R_1 + R_2)^2}{R_1 \cdot R_2} \cdot (T_t - T_b) \cdot \left[ K_e + \frac{K_i \cdot K_m}{(K_i + K_m)} \right]$$

where:

R is the resistance of resistor 18;
$R_1$ is the resistance of resistor 26;
$R_2$ is the resistance of resistor 24;
G is a geometrical constant of the katharometer based on the geometry of the inner cell and of the filament or thermistor and its disposition in the cell;
$T_t$ is the temperature of the element 10;
$T_b$ is the temperature of the katharometer body;
$K_1$ is an equivalent gas thermal conductivity corresponding to the heat loss (leakage) by the thermistor electrical leads;
$K_i$ is the equivalent gas thermal conductivity corresponding to the thermal resistivity of the element 10; and
$K_m$ is the thermal conductivity of the gas to be determined.

This equation contains a thermal model describing the operation of the katharometer circuit just described and can be regarded as comprising three parts. The left hand part involving resistance values describes the electrical dependence of the configuration of the circuit. The centre part involving temperature values embodies an important consequence of the fact that the value of $T_t$ is constant, which means that either $T_b$ must be known accurately, using an independent measuring instrument such as a thermometer, or the ratio of two measurements taken very close together in time is used, when $T_b$ has not changed substantially if at all and this factor can be eliminated from the final result. The right hand part of the equation describes a specific simplified but sufficiently accurate thermal model of the operation of the katharometer. One of the parameters is the unknown value $K_m$ to be measured, and it is necessary therefore to obtain suitable values for $K_i$ and $k_1$; these are obtained from measurements of any three known gases, preferably nitrogen, argon and helium (or hydrogen) made at a given temperature, the values being obtained from the ratio of the resultant $V_o$ values.

Since the left hand part of the relation is dependent upon the specific electrical circuit of the katharometer it can itself be regarded as a circuit constant, when the relation will have the more general form below that is applicable also to other types of katharometer:

$$\text{POWER} = \frac{1}{G} \cdot (T_t - T_b) \cdot \left[ K_e + \frac{K_i \cdot K_m}{(K_i + K_m)} \right]$$

The total electric power that is supplied to the element 10 can be determined by the relation:

$$\text{POWER} = \frac{V_0^2}{R} \cdot \frac{R_1 \cdot R_2}{(R_1 + R_2)^2}$$

Since it is the amount of power (energy per second) that is supplied to the element 10 that maintains its temperature, either the voltage or the current can be measured to obtain a measurement representative of the gas thermal conductivity, since all of the resistances in the circuit are known and are of constant value, the measurement of the voltage usually being preferred.

Figure 2:
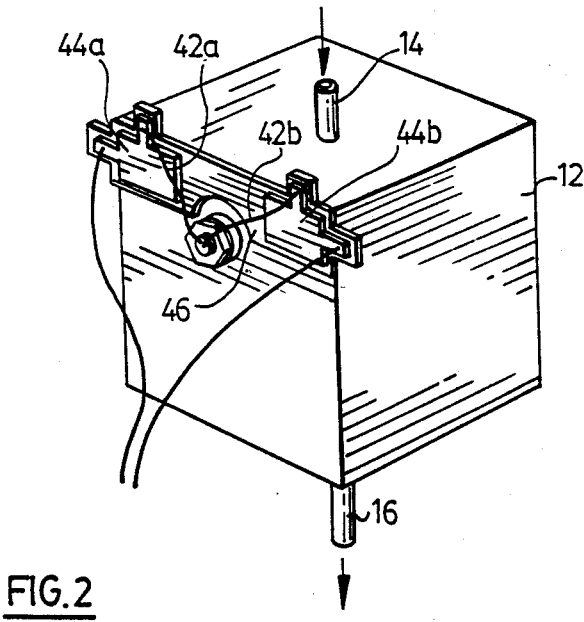
FIG. 2 is a diagrammatic view of a temperature sensitive element illustrating the use of isothermal heat sink plates to stabilize the temperature of its leads.

The value of $K_1$ can be kept at a substantially constant value by the arrangement illustrated by FIG. 2, in which the lead wires 42a and 42b to the element 10 are kept as short as possible and welded independently to respective isothermal heat sinks 44a and 44b, constituted in this embodiment by copper plates, the plates being cemented to a support block 46 attached to the enclosure 12 and electrically insulated from the enclosure and from one another. It will be noted that it is immaterial whether $V_o$ is positive or negative, and this has no effect on the measurement of $K_m$, since the term $V_o^2$ appears in the relation (1). In a specific embodiment the element 10 was a thermistor obtained from Gow-Mac Corporation, having an internal resistance of 8 Kohm at 25° C. The value of R was 1K and that of $R_1$ and $R_2$ was 10K all three being metal film type of 1% tolerance with thermal coefficient of ±50 ppm per °C. The value of resistor 38 was 22K. The amplifier was type LT10131AM and the values of V+ and V+ were respectively +15 and −15 volts.

In using the apparatus to measure the percentage of hydrogen in liquid aluminum pure nitrogen is first injected through the katharometer into a probe immersed in the aluminum and a first reading of $V_o$ is taken. The gas is then circulated continuously between the probe and katharometer in a closed circuit while hydrogen from the aluminum accumulates in the nitrogen carrier gas until equilibrium is reached, based on the respective partial pressures, this usually taking about ten minutes; a second reading is then taken, from which the gas thermal conductivity is determined. This is also the operating procedure used with prior art apparatus. During this relatively long period the temperature of the block 38 can change by several degrees, with the result that the first reading is no longer a valid zero reading.

Accordingly in a method of the invention a first reading is taken after the carrier nitrogen has been circulated until the equilibrium with the entrained hydrogen is obtained; immediately after taking this reading pure nitrogen is injected into the circuit to purge the cell of the gas mixture and a second reading is taken about 10–30 seconds, preferably about 15–20 seconds after the first reading. The katharometer body is a relatively large heat sink and any changes in its temperature therefore take place very slowly. The hydrogen concentration is determined by calculation from the two closely-timed thermal conductivity readings that are obtained; since the temperature differences are minimized the precision of measurement is increased.

The new apparatus thus uses a single thermal element and precision can be maintained even with changes in the ambient temperature of the katharometer between 10° C. and 60° C., and this precision can be obtained by use of a single measurement provided the temperature of the katharometer body is known to within 0.01° C., or if two readings are compared as just described above. It will be seen in particular that the control of the temperature of the element 10 is simple in that it is only necessary to control its electrical resistance; the device can be operated at any convenient temperature above the gas temperature within its normal temperature range and it is only necessary for it to be maintained constant at that temperature.

The lower thermal conductivity values can be measured with absolute precision to within ±0.03%. The corresponding precision of percentage of hydrogen in the hydrogen/nitrogen gas mixture is about 1% relative on a 1% hydrogen mixture. The signal level obtainable is dependent on the resistance values of the components, particularly that of the thermistor, and is independent of the resistance/temperature characteristic. Thermistors are particularly suitable for use as the element 10, since in general their resistance correlates accurately and uniformly with their corresponding operating temperature and they are available with a wide range of temperature/resistance characteristics. It is also possible to measure the higher values (up to 100% hydrogen) with adequate dynamic signal range and without saturation of the associated amplifier With prior art apparatus a substantial inaccuracy was caused by the fact that the measurements were made at temperatures which were not necessarily constant from measurement to measurement, and the thermal conductivities of all gases change with temperature; with the methods and apparatus of the invention the measurements are effectively ratios at the same temperature and these differences therefore disappear to make the measurements virtually temperature insensitive over the operating range.

Figure 3:
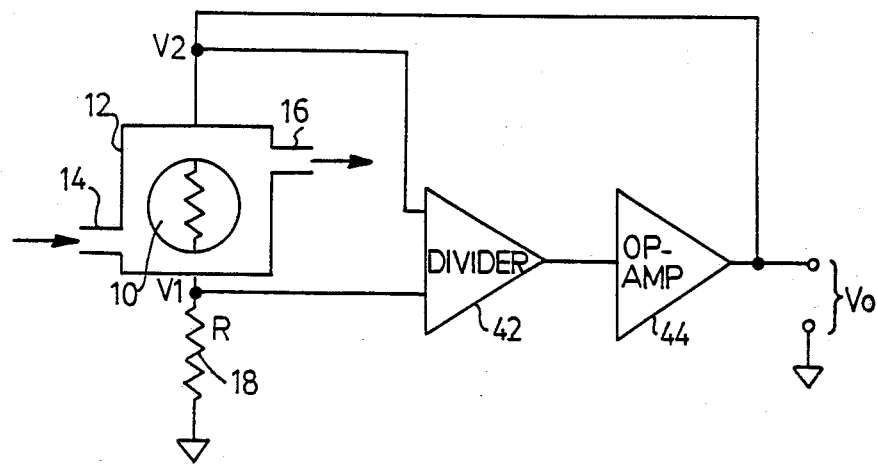
FIG. 3 is a schematic circuit diagram of a second embodiment.

In the circuit of FIG. 3 the same or a similar element is given the same reference number, wherever that is possible. Thus the thermistor element 10 is connected in series with a resistor 18, and is connected across the input of a divider 42 whose inputs are the potential $V_1$ and $V_2$ at the terminals of the element, and whose output is $V_2/V_1$, this output being fed to an operational amplifier 44. The value of resistor 18 is set to give a desired value (e.g. 2) to this ratio at the predetermined operating temperature and resistance of the element, and the power output of amplifier 44 is sufficient to maintain the ratio stable at that value. As the thermistor 10 cools and its resistance decreases the value of the ratio decreases, whereupon the output of amplifier 44 increases to heat the element and restore the resistance to its original equilibrium value. The value of $V_0$ is measured at the output of the amplifier 44.

We claim:

1. A method for the measurement of gas thermal conductivity employing a katharometer including:
   supplying electric power to a single katharometer element having a temperature/resistance characteristic to heat it to a predetermined temperature value and a corresponding resistance value;
   passing a test gas whose thermal conductivity is to be measured over the katharometer element to thereby change its temperature from the predetermined value and its resistance from the corresponding value;
   employing the change of resistance of the element to change the supply of electrical power to the element to restore its temperature to the predetermined value and its resistance to the corresponding value; and
   measuring the amount of power supplied to the element with its temperature restored to the predetermined value to determine the test gas thermal conductivity;
   wherein the test gas whose conductivity is to be measured is entrained in a carrier gas;
   the method employing two measurements spaced in time to determine the proportion of the test gas entrained in the carrier gas;
   the method including circulating the carrier gas through the katharometer element and a probe in contact with the test gas for a first period of time sufficient to entrain the test gas in the carrier gas to form a mixture of gases, and thereafter making a first measurement;
   thereafter purging the katharometer with carrier gas to remove the gas mixture and making a second measurement within a short period of time after the first measurement; and
   employing the first and second measurements to eliminate the temperature of the katharometer element body as a variable from the gas thermal conductivity measurement.

2. A method as claimed in claim 1, wherein the element is connected in series with a resistor to provide a first potential divider having a respective first junction; the potential at the first junction is compared with that at the junction of a second potential divider; and the result of the comparison is employed to change the supply of electrical power to the element.

3. A method as claimed in claim 2, wherein the potentials at the first and second potential divider junctions are compared by a differential amplifier, the output of which controls the supply of electrical power to the element.

4. A method as claimed in claim 3, wherein the voltage at the differential amplifier output is measured to determine the gas thermal conductivity.

5. A method as claimed in claim 1, wherein the test gas is removed from a molten metal by entrainment in the carrier gas.

6. A method as claimed in claim 5, wherein the test gas is hydrogen and the molten metal is aluminum.

7. A method as claimed in claim 1, including passing a reference gas over the katharometer element while it is heated to establish the predetermined temperature value and the corresponding resistance value.

8. Apparatus for the measurement of gas thermal conductivity of a test gas comprising:
   a single katharometer element having a temperature/resistance characteristic;
   means for passing a reference gas over the element;
   means for supplying electric power to the element to heat it to a predetermined temperature value and a corresponding resistance value;
   means for supplying the test gas whose conductivity is to be measured to the single element to thereby change the temperature of the element from the predetermined value and thereby change its resistance from the corresponding value;
   control means responsive to the change of resistance of the single element to change the amount of electric power supplied to the element to maintain its temperature at the predetermined value and its resistance at the corresponding value; and
   means for measuring the amount of power required to maintain the element at its predetermined temperature in the presence of the test gas to provide a measurement representative of the thermal conductivity of the gas;
   wherein the element has electrical leads and the leads are mounted on respective thermal heat sinks to stabilize the leakage thermal resistance thereof.

9. Apparatus as claimed in claim 8, wherein the control means comprise a resistance connected in series with the element to constitute a first potential divider having a first junction, a second potential divider having a second junction, and a differential amplifier having tow inputs supplied from the respective junctions, the output of the amplifier being connected to the element to control the amount of the electric power supplied to the element.

10. Apparatus as claimed in claim 9, wherein the voltage at the amplifier output is measured and is representative of the thermal conductivity of the test gas.

11. Apparatus as claimed in claim 8, and comprising means for supplying a reference gas to the katharometer element while it is heated to establish the predetermined temperature value and the corresponding resistance value.

12. A katharometer comprising a single katharometer element having a temperature/resistance characteristic and having electrical leads for connection to a power source for the supply of electric power to the single element to heat it to a predetermined operating temperature, wherein heat leakage from the leads will have the equivalent effect as a change in thermal conductivity of a gas supplied to the element and will therefore affect the sensitivity of measurement by the katharometer, and wherein the leads are mounted on respective isothermal heat sinks to stabilize the leakage thermal resistance thereof.

13. A katharometer as claimed in claim 12, wherein the isothermal heat sinks are metal plates.

14. A method of operating a katharometer employing two measurements spaced in time to determine the proportion of gas dissolved in molten metal, the method including circulating a carrier gas through the katharometer and a probe immersed in the molten metal for a first period of time sufficient to entrain the gas to be determined in the carrier gas to form a mixture of gases, and thereafter making a first measurement;

and thereafter purging the katharometer with carrier gas to remove the gas mixture and making a second measurement within a short period of time after the first measurement.

15. A method as claimed in claim 14, wherein the first period of time is of the order of about 10–15 minutes and the second period of time is of the order of 10–30 seconds, preferably 15–20 seconds.

16. A method of operating a katharometer to obtain the thermal conductivity Km of gas, the katharometer employing an element having a temperature/resistance characteristic and that is exposed to the cooling effect of the gas, comprising the step of measuring the power required to maintain the element at a predetermined temperature and then determining the value of Km by the relation:

$$\text{POWER} = \frac{1}{G} \cdot (T_t - T_b) \cdot \left[ K_e + \frac{K_i \cdot K_m}{(K_i + K_m)} \right]$$

where:
G is a geometrical constant of the katharometer;
$T_t$ is the temperature of the element;
$T_b$ is the temperature of the katharometer body;
$K_1$ is an equivalent gas thermal conductivity corresponding to heat loss by the element electrical leads;
$K_i$ is the equivalent gas thermal conductivity corresponding to the thermal resistivity of the element; and
$K_m$ is the thermal conductivity of the gas to be determined.

17. A method as claimed in claim 16, wherein the value of $T_b$ is obtained by independent measurement and a single measurement is employed to obtain the value of Km.

18. A method as claimed in claim 16, wherein two measurements are made sufficiently closely spaced in time for $T_b$ to be substantially constant, and the two measurements are employed to obtain the value of Km with elimination of the variable $T_b$.

* * * * *